US005529783A

United States Patent [19]
Burke et al.

[11] Patent Number: 5,529,783
[45] Date of Patent: Jun. 25, 1996

[54] ROTOR GRANULATION AND COATING OF ACETAMINOPHEN, PSEUDOEPHEDRINE, CHLORPHENIRAMINE, AND, OPTIONALLY DEXTROMETHORPHAN

[75] Inventors: Gerald M. Burke, North Wales; John W. Scott, III, West Chester, both of Pa.

[73] Assignee: McNeil-PPC, Inc., Milltown, N.J.

[21] Appl. No.: 359,108

[22] Filed: Dec. 19, 1994

[51] Int. Cl.$^6$ .................................................. A61K 9/20
[52] U.S. Cl. ........................ 424/441; 424/464; 424/489; 514/974
[58] Field of Search ................................ 424/441, 464, 424/489

[56] References Cited

U.S. PATENT DOCUMENTS

| | | | |
|---|---|---|---|
| 4,800,087 | 1/1989 | Mehta | 424/497 |
| 4,971,791 | 11/1990 | Tsau et al. | 424/81 |
| 5,075,114 | 12/1991 | Roche | 424/470 |
| 5,084,278 | 1/1992 | Mehta | 424/441 |
| 5,215,755 | 6/1993 | Roche et al. | 424/480 |
| 5,260,072 | 11/1993 | Roche et al. | 424/464 |

FOREIGN PATENT DOCUMENTS

| | | |
|---|---|---|
| 0473431A1 | 3/1992 | European Pat. Off. . |
| 0523847A1 | 1/1993 | European Pat. Off. . |
| 0538034A1 | 4/1993 | European Pat. Off. . |

*Primary Examiner*—Thurman K. Page
*Assistant Examiner*—James M. Spear
*Attorney, Agent, or Firm*—Bernard F. Plantz

[57] ABSTRACT

Chewable tablets comprising individual taste-masked coated granules comprising an analgesic and at least one water soluble medicament and methods of producing the same are described.

12 Claims, No Drawings

ROTOR GRANULATION AND COATING OF ACETAMINOPHEN, PSEUDOEPHEDRINE, CHLORPHENIRAMINE, AND, OPTIONALLY DEXTROMETHORPHAN

FIELD OF THE INVENTION

This invention relates to chewable tablets containing more than one active medicament, maintaining good taste and mouth-feel.

BACKGROUND OF THE INVENTION

Orally administered medicaments are given to the patient in many forms, such as liquid solutions, emulsions, or suspensions, or in solid form such as capsules or tablets (as used herein, the term "tablet" means any shaped and compressed solid dosage form, including caplets). Medicaments administered in tablet or capsule form are usually intended to be swallowed whole. Therefore, the often disagreeable taste of the active ingredient need not be taken into account in formulating the dosage form, except for the provision of means to prevent the taste from being apparent during the short time that the dosage form is in the mouth. Such means may include the use of an appropriately thin and quickly dissolving coating on the tablet, the use of the gelatin capsule form, or simply compressing a tablet firmly so that it will not begin to disintegrate during the short time that it is intended to be in the mouth.

It is desirable to provide the medicine either in liquid form or in a chewable solid form for children, especially toddlers, older persons, and many other persons, that have trouble swallowing whole tablets and capsules. Even where the medicine can be formulated as a liquid, it is desirable also to be able to provide a chewable solid form for convenience.

A common problem with chewable tablet forms is the often disagreeable taste of the active ingredient which manifests itself during chewing. In some cases, the taste of the active medicament in a tablet can be masked by adding flavoring ingredients to the tablet.

A different approach was taken with a children's size tablet containing acetaminophen (acetyl para-amino phenol or "APAP"). A children's size tablet of APAP is available commercially wherein the APAP is present in granules that are coated with ethyl cellulose. A significant proportion of the APAP remains shielded by the coating (and therefore does not contribute to taste) while the tablet is in the mouth, despite some breakage of the ethyl cellulose coating during compression of the tablet and some additional breakage of the coating during chewing. The APAP becomes available via permeation through the coating (although ethyl cellulose is not soluble in aqueous fluids, water does permeate through the coating) and from the granules wherein the coating was broken.

U.S. Pat. No. 5,075,114 issued to Edward J. Roche on Dec. 24, 1991 (incorporated herein by reference), describes chewable tablets prepared by coating compressed granulated active acetaminophen, using fluidized bed coating. Combinations of two or more of pseudoephedrine HCl, chlorpheniramine maleate, dextromethorphan HBr, diphenhydramine HCl or citrate, acetaminophen, ibuprofen, and naproxen are contemplated, but it is also suggested that coatings may be varied to provide a slower release of one medicament over another, indicating discrete granules of each medicament. The coatings comprised about 5 to about 28% of the total dry weight of the granule and comprised a polymer blend.

U.S. Pat. No. 5,260,072 issued to Edward J. Roche, et al. on Nov. 9, 1993 (incorporated herein by reference) describes rotor granulations and tastemasking coatings comprising polymer blends of one or both of cellulose acetate or cellulose acetate butyrate and polyvinylpyrrolidone. The inclusion of two or more medicaments is contemplated, but it is also indicated that the coatings for each medicament can be varied, suggesting discrete granules of each medicament.

Commonly assigned copending application Ser. No. 08/166 111, filed Dec. 13, 1993, now U.S. Pat. No. 5,489,436 to Michael R. Hoy, et al. (incorporated herein by reference) describes chewable tablets comprising rotor granules coated with polymer blends including cellulose acetate and methyl aminoethyl methacrylate neutral methacrylic acid ester (the preferred representative compound being Eudragit® E-100). The coating method described is fluid bed coating. The inclusion of two or more medicaments is contemplated, but not described by example.

A need remains for a chewable tablet comprising more than one active ingredient without sacrificing taste. This is particularly important for children.

SUMMARY OF THE INVENTION

In one aspect, the present invention relates to chewable tablets containing a solid analgesic and at least one other medicament which is soluble in water. The analgesic and the other medicaments(s) are granulated together with a binder to form individual granules comprising all the active ingredients. The granules are coated with a taste-masking composition. The tablet contains the coated granules, sweeteners, flavoring, and, optionally, other excipients.

In another aspect, the present invention relates to chewable tablets containing a solid analgesic and at least one other medicament which is soluble in water produced by a process by which the solid analgesic and water soluble medicament(s) are granulated together with a binder, coated with a taste-masking composition, and then blended and compressed with sweeteners, flavoring, and, optionally, other excipients.

In a further aspect, the present invention relates to a process for preparing chewable tablets containing more than one medicament. According to the process of the invention, a solid analgesic is granulated with at least one other water soluble medicament and a binder. The granules are then coated with a taste-masking composition, and blended and compressed with sweeteners, flavoring, and, optionally, other excipients.

DETAILED DESCRIPTION

The invention will now be described specifically in terms of its most preferred embodiments. Reference will also be made in detail herein to other preferred embodiments of the compositions, processes, and methods of the invention. The tablets according to the invention are prepared by granulation of a solid analgesic with one or more water soluble active ingredients and a binder, coating the resultant actives granulation with a taste-masking composition, and then combining the coated granulation with other excipients, such as sweeteners, flavoring agents, extenders, and the like, and compressing into tablet form. The taste-masking provided by the coating helps limit the quantity of other flavoring agents and sweeteners necessary in the tablet to mask the unpleasant flavor of the medicament.

The tablets according to the invention preferably contain three active ingredients or medicaments, an analgesic, antihistamine, and decongestant, and pharmaceutically acceptable salts thereof. In addition to the foregoing, the tablets can also contain a cough suppressant, and pharmaceutically acceptable salts thereof.

In a preferred embodiment, the tablets according to the invention contain acetaminophen as the analgesic, chlorpheniramine maleate as the antihistamine, and pseudoephedrine HCl as the decongestant. In a further preferred embodiment, the tablets additionally contain dextromethorphan HBr as the cough suppressant.

Depending on whether a children's regular strength or adult strength dosage is desired, the dosage form will generally contain from about 80 to about 500 mg of acetaminophen, about 0.5 to about 2 mg of chlorpheniramine maleate, about 7.5 to about 30 mg of pseudoephedrine HCl and, optionally, about 5 to about 15 mg of dextromethorphan HBr. The dextromethorphan HBr may be used in its salt form or as a 10% (wt.) adsorbate.

The active ingredients can be granulated together using, for example, a rotor granulator. A rotor granulator produces nearly spherical granulated particles which have increased strength and resistant to breakage due to the densification of the granulation mixture as the roto granules are formed in the rotor granulator fluid bed. This resistance to breakage can be advantageous when preparing tablets containing more than one active ingredient since broken particles are smaller and irregular in shape, they may not be readily coated in subsequent coating steps. This can detract from the taste-masking purpose of coating. However, other granulating methods, such as top spray and high shear granulation, are also contemplated. The granulated particles are preferably in the size range of from about 125 to about 850 microns. Generally, particles of like size facilitate blending and provide regularity to dosage forms.

The analgesic and, optionally, the cough suppressant (both in particle form) are fluidized in the rotor granulator. Then a granulating solution containing the water soluble active(s), a binder(s), and solvent(s), generally water, alcohol or mixtures thereof, are sprayed onto the fluidized particles and then dried to form the actives granulation. The granulating solution generally comprises from about 1 to about 20% by weight of the binder. Suitable binders for use in the granulating solution include starch, pregelatinized starch, gelatin, polyvinylpyrrolidone, methylcellulose, hydroxypropyl methylcellulose, sodium carboxymethylcellulose, ethyl cellulose, polyacrylamides, polyvinyloxazolidone and polyvinyl alcohols.

The granulated particles are then coated with a taste masking composition, for example, in a fluid bed rotor. Other coating methods, such as a Wurster or top spray fluid bed coating process, are also contemplated. In the tablets according to the invention, it is desirable that all particles are coated uniformly throughout the particle surface and to the same extent.

The coated particles or granules are then dried. Drying can be performed in a fluid bed rotor unit, or by other suitable means.

Granulating and coating methods are disclosed in, for example, Jones, D.M., "Factors to Consider in Fluid-Bed Processing", *Pharmaceutical Technology*, April, 1985 and Jager, F.F., et al., "Effect of Material Motion on Agglomeration in the Rotary Fluidized-Bed Granulator," *Drugs Made in Germany*, Vol. XXV, pp. 61–65 (1982) (both incorporated herein by reference).

A solids taste-masking composition is generally used for coating the granulated particles. In a preferred embodiment, a combination of cellulose acetate and methylaminoethyl methacrylate neutral methacrylic acid ester (MM/MAE, i.e., Eudragit® E 100), in a ratio of 65:35, respectively, is used. Generally, the particles are coated with from about 8 to about 20 percent of the polymer, based on the total particle weight.

Other coating materials which can be utilized include polymer compositions including cellulose acetate (CA), or cellulose acetate butyrate (CAB), polyvinylpyrrolidone (PVP), cellulose triacetate powder (CAT), hydroxypropyl cellulose (HPC), hydroxyethyl cellulose (HEC) and methylaminoethyl methacrylate and neutral methacrylic acid ester (MM/MAE), and mixtures thereof.

When CA or CAB is utilized, it is preferable that PVP is added to the coating mixture to provide bioavailability. CA and CAB are quite water insoluble. The preferred ratio of CA and/or CAB to PVP is from about 95:5 to about 60:40.

Those polymer coatings which are not water soluble can be solubilized in organic solvents for use in coating. A wide variety of organic solvents can be used. For instance, acetone, methanol, methylene chloride, ethyl acetate, toluene ethanol, and others. A suitable solvent system can be readily ascertained by one skilled in the art. The proportion of the polymer in the coating solution will generally range from about 5 to about 20% by weight.

A tablet blend is then prepared comprising the coated particles, sweetener, flavoring, and other excipients. After blending, the tablet is compressed in the presence of a lubricant (to lubricate the dye walls and punches used during the tablet compression procedure) to a target hardness of from about 5.0 to about 8.0 kp and a friability of from about 0 to about 1%.

The several ingredients and some typical replacements for them are as follows:

Mannitol can be used as a natural sweetener. It can be replaced by dextrose, fructose, sorbitol, compressible sugar, or lactose.

Artificial sweeteners, such as aspartame and saccharin, can be used in combination with natural sweeteners.

Any pharmaceutically acceptable flavoring agent, natural, artificial, or mixtures thereof, is suitable for use in the dosage form.

The lubricant can be colloidal silicon dioxide, magnesium stearate, stearic acid, talc, calcium stearate, zinc stearate, leucine, glycerides, sodium stearyl fumarate, or combinations thereof.

The examples below set forth the ingredients and proportions for typical laboratory scale preparation.

Example 1

Chewable children's tablets with cough suppressant were prepared. The formulations in unit weight (mg/tablet) and batch weight (gram/preparation) are presented below in Table I. In this example, the analgesic utilized was acetaminophen. The decongestant was pseudoephedrine HCl (PE) and the antihistamine was chlorpheniramine maleate (CM). The cough suppressant dextromethorphan HBr was utilized in the form of 10% (wt) adsorbate.

TABLE I

| Ingredients | Unit wt. (mg) |
|---|---|
| Acetaminophen USP (Powdered) | 80.0 |
| Dextromethorphan HBr 10% (Adsorbate) | 25.0 |
| Pseudoephedrine HCl USP | 7.5 |
| Chlorpheniramine Maleate USP | 0.5 |
| Hydroxypropyl Methylcellulose 2910 USP | 0.5 |
| Purified Water USP | — |
| *Rotor Coating* | |
| Rotogranulated Actives | 113.25 |
| Acetone NF | (113.25) |
| Eudragit ® E 100 | 5.41 |
| Cellulose Acetate NF, 398-10 | 10.04 |
| *Blending and Compression* | |
| Dye Blend | |
| Mannitol USP (Granular, FL-2080) | 72.00 |
| Aspartame NF | 6.57 |
| Colorant | 0.039 |
| Mannitol USP (Granular, FL-2080) | 229.84 |
| Stearic Acid NF | 4.80 |
| Colloidal Silicon Dioxide NF | 2.40 |
| Actives Granulation | 123.79 |
| Flavor | 4.56 |
| Microcrystalline Cellulose NF, Avicel PH101 | 36.00 |
| Total | 480.0 |

The CM was dissolved in the purified water, PE was added, followed by HPMC, to form the granulating solution, which contained about 70% (wt.) of water. A Glatt GRG-200 rotor granulator was then charged with the acetaminophen and dextromethorphan HBr adsorbate, in that order. The granulating solution was sprayed onto the fluidized acetaminophen and dextromethorphan HBr adsorbate particles and additional purified water was added as necessary to achieve the desired particle size the rotor granulation was then dried and sieved. MM/MAE was dissolved in acetone in a stainless steel container, and cellulose acetate was added to this mixture to form a polymer solution. The ratio of MM/MAE to cellulose acetate was 35:65. The rotor granulator was then charged with the actives granulation and coating was performed. Rotor granules were about 12% (wt.) coated upon completion of the coating process and utilized of the materials listed in Table I. Coated particles were then dried and sieved.

Blending and compression were then performed in the usual manner. A dye blend was prepared using a portion of the mannitol, aspartame, and colorant. The dye blend was then combined with the coated particles, stearic acid, colloidal silicon dioxide, the remaining mannitol, flavoring, and microcrystalline cellulose to form a final blend. The final blend was then compressed to achieve a final tablet weight of 480 mg. Tablets so produced have a diameter of 13/32 inch, hardness of from about 5 to about 10 kp, friability of from about 0 to about 1%, and thickness of from about 4.5 to about 5 mm.

Example 2

The same procedure as in Example 1 was carried out, using dextromethorphan HBr in place of the 10% adsorbate. The formulation is presented in Table II below.

TABLE II

| Ingredient | Formulation mg/tab |
|---|---|
| *Rotor Granulation* | |
| Acetaminophen USP | 80.0 |
| Chlorpheniramine Maleate USP | 0.5 |
| Pseudoephedrine HCl USP | 7.5 |
| Dextromethorphan HBr (10% adsorbate) | — |
| Dextromethorphan HBr | 2.5 |
| Hydroxypropyl Methylcellulose 2910 USP | 0.5 |
| Purified Water USP | (—) |
| *Rotor Coating* | |
| Actives Granulation | 91.0 |
| Cellulose Acetate NF 398-10 | 8.1 |
| Eudragit E-100 | 4.3 |
| Acetone NF | (91.0) |
| *Blending and Compression* | |
| Aspartame NF | 6.6 |
| Colorant | 0.04 |
| Mannitol USP (Granular, FL-2080) | 322.2 |
| Colloidal Silicon Dioxide NF | 2.4 |
| Stearic Acid NF | 4.8 |
| Actives Granulation (Coated) | 103.4 |
| Flavor | 4.6 |
| Microcrystalline Cellulose NF (Avicel PH101) | 36.0 |
| Total | 480.0 |

Example 3

The same procedure as in Example 1 is followed, without any dextromethorphan HBr. The formulation is presented in Table III below.

TABLE III

| Ingredient | Formulation mg/tab |
|---|---|
| *GRANULATION* | |
| Acetaminophen USP | 80.0 |
| Chlorpheniramine Maleate USP | 0.5 |
| Pseudoephedrine HCl USP | 7.5 |
| Hydroxypropyl Methylcellulose 2910 USP | 0.5 |
| *ROTOR COATING* | |
| Actives Granulation | 88.5 |
| Cellulose Acetate NF 398-10 | 7.9 |
| Eudragit E-100 | 4.2 |
| Acetone NF | (100.6) |
| *BLENDING AND COMPRESSION* | |
| Aspartame NF | 11.0 |
| Colorant | 0.66 |
| Mannitol USP (Granular, FL-2080) | 318.4 |
| Colloidal Silicon Dioxide NF | 2.4 |
| Stearic Acid NF | 4.8 |
| Magnesium Stearate NF | — |
| Actives Granulation | 100.6 |
| Citric Acid USP (Anhydrous Powder) | 3.1 |
| Flavors | 3.1 |
| Microcrystalline Cellulose NF (Avicel PH101) | 36.0 |
| Total | 480.0 |

The scope of the present invention is not limited by the description, examples, and suggested uses herein and modifications can be made without departing from the spirit of the invention. For example, other components may be added to the tablets including additional actives, various flavorings, preservatives and other pharmaceutical excipients.

Application of the compositions and processes of the present invention for medical and pharmaceutical uses can be accomplished by any clinical, medical and pharmaceutical methods and techniques as are presently and prospectively know to those skilled in the art. Thus, it is intended that the present invention cover the modifications and variations of this invention provided that they come within the scope of the appended claims and the their equivalents.

What is claimed is:

1. A chewable tablet comprising solid acetaminophen and at least one water soluble medicament produced by a process comprising the steps of
   a) fluidizing solid acetaminophen;
   b) spraying a granulating solution comprising said at least one water soluble medicament and a binder onto said fluidized solid acetaminophen to form an actives granulation;
   c) drying said actives granulation;
   d) coating said actives granulation with a taste-masking composition to form coated granules;
   e) blending said coated granules with excipients; and
   f) compressing to form a tablet.

2. The chewable tablet of claim 1 wherein said at least one water soluble active is selected from the group consisting of an antihistamine, a decongestant, and a cough suppressant, and combinations thereof.

3. The chewable tablet of claim 1 comprising an antihistamine and decongestant.

4. The chewable tablet of claim 2, further comprising the step of fluidizing a solid cough suppressant with said acetaminophen.

5. The chewable tablet of claim 4 comprising acetaminophen, chlorpheniramine, pseudoephedrine, and dextromethorphan, or salts thereof.

6. The chewable tablet of claim 5 wherein said acetaminophen is present in a dosage of from about 80 to about 500 mg, said chlorpheniramine maleate is present in a dosage of from about 0.5 to about 2 mg, said pseudoephedrine HCl is present in a dosage of from about 7.5 to about 30 mg, and said dextromethorphan HBr is present in a dosage of from about 5 to about 15 mg.

7. A process for producing a chewable tablet comprising solid acetaminophen and at least one water soluble medicament comprising the steps of
   a) fluidizing solid acetaminophen;
   b) spraying a granulating solution comprising said at least one water soluble medicament and a binder onto said fluidized solid acetaminophen to form an actives granulation;
   c) drying said actives granulation;
   d) coating said actives granulation with a taste-masking composition to form coated granules;
   e) blending said coated granules with excipients; and
   f) compressing to form a tablet.

8. The process of claim 7 wherein said at least one water soluble active is selected from the group consisting of an antihistamine, a decongestant, and a cough suppressant, and combinations thereof.

9. The process of claim 7 comprising an antihistamine and decongestant.

10. The process of claim 9, further comprising the step of fluidizing a cough suppressant with said solid acetaminophen.

11. The process of claim 10 comprising acetaminophen, chlorpheniramine, pseudoephedrine, and dextromethorphan, or salts thereof.

12. The process of claim 11 wherein said acetaminophen is present in a dosage of from about 80 to about 500 mg, said chlorpheniramine maleate is present in a dosage of from about 0.5 to about 2 mg, said pseudoephedrine HCl is present in a dosage of from about 7.5 to about 30 mg, and said dextromethorphan HBr is present in a dosage of from about 7.5 to about 15 mg.

* * * * *